United States Patent
Bacot et al.

[11] Patent Number: 6,074,830
[45] Date of Patent: Jun. 13, 2000

[54] 3,4-DIHYDROXY-2-BUTANONE 4-PHOSPHATE SYNTHASE

[75] Inventors: Karen Onley Bacot, Landenberg, Pa.; Douglas Brian Jordan; Paul Veikko Viitanen, both of Wilmington, Del.

[73] Assignee: E. I. du Pont de Nemours & Company, Wilmington, Del.

[21] Appl. No.: 09/094,148

[22] Filed: Jun. 9, 1998

[51] Int. Cl.[7] .............. C12Q 1/68; C12N 9/16; C12N 1/20; C07H 21/04
[52] U.S. Cl. .......... 435/6; 435/196; 435/252.33; 435/419; 536/23.2
[58] Field of Search .............. 536/23.2; 435/6, 435/196, 252.33, 419

[56] References Cited

U.S. PATENT DOCUMENTS 5,821,090  10/1998  Revuelta Doval et al. .............. 435/88

FOREIGN PATENT DOCUMENTS 4420785  3/1994  Germany ................... C12N 15/80
WO 94/11515  of 0000  WIPO .

OTHER PUBLICATIONS

Richter et al., *J. Bacteriol.*, 174, 4050–4056, 1992.
Santos et al., *J. Biol. Chem.*, 270, 437–444, 1995.
F. Muller, *Chemistry and Biochemistry of Flavoenzymess*1, 215–259, 1991.
Swartzman et al., *J. Biol. Chem.*, 265, 3513–3517, 1989.
Lee et al., *J. Bacteriol.*, 176, 2100–2104, 1994.
Kil et al., *Mol. Gen. Genet.*, 233, 483–486, 1992.
Gusarov et al., *Mol. Biol*, vol. 31, p. 370–376, 1997.
Fuller et al., *J. Bacteriol.*, 177, 7265–7270, 1995.
Kobayashi et al., *Gene*, 160, 303–304, 1995.
Garcia–Ramirez et al., *J. Biol. Chem.*, 270, 23801–23807, 1995.
Watson, et al. Recombinant DNA, 2nd edition. W.H. Freeman and Company, New York. pp. 100–102 and 273–292, Feb. 14, 1994.
Howard et al. Breaking and entering: host penetration by the fungal rice blast pathogen Magnaporthe grisea. Annnu. Rev. Microbiol. 50:491–512, 1996.

*Primary Examiner*—Robert A. Wax
*Assistant Examiner*—Devesh Srivastava

[57] ABSTRACT

Through functional complementation of an *Escherichia coli* auxotroph, 3,4-dihydroxy-2-butanone 4-phosphate synthase (DS), an indispensable enzyme of the riboflavin biosynthetic pathway of the rice blast fungus *Magnaporthe grisea*, has been cloned. This invention relates to the isolation of the nucleic acid fragment that encodes the fungal DS protein. In addition, the invention also relates to the construction of chimeric genes encoding all or a portion of the *Magnaporthe grisea* DS protein, in sense or antisense orientation, wherein the expression of the chimeric gene results in production of altered levels of *Magnaporthe grisea* DS in a transformed host cell. Finally, the invention also relates the use of the *Magnaporthe grisea* DS protein as a tool for identifying chemical agents that could be useful as fungicides, antibiotics, or herbicides.

11 Claims, 1 Drawing Sheet

```
           1                                                                    50
E. coli    -MNQTLLSSF GTPFERVENA LAALREGRGV MVLDDEDREN EGDMIFPAET
V. harv.   MSSTSLLDEF GTPVQRVERA IEALKNGLGV LLMDDEDREN EGDLIFSAQH
S. cere.   ---------- --MFTPIDQA IEHFKQNKFV IVMDDAGREN EGDLICAAEN
A. goss.   ---------M TSPCTDIGTA IEQFKQNKMI IVMDHISREN EADLICAAAH
M. gris.   --MPSTDSIP KSNFDAIPDV IQAFKNGEFV VVLDDPSREN EADLIIAAES 51                                                                   100
E. coli    MTVEQMALTI RHGSGIVCLC ITEDRRKQLD LPMMV..... .ENNTSAYGT
V. harv.   LTEAQMALMI REGSGIVCLC LTEERANWLD LPPMV..... .KDNCSKNQT
S. cere.   VSTEQMAFLV RHSSGYVCAP MTNAIADKLD LPLLRTGMKF ESNDDDRHGT
A. goss.   MTAEQMAFMI RYSSGYVCAP MTNAIADKLD LPLMNT.LKC KAFSDDRHST
M. gris.   VTTEQMAFMV RHSSGLICAP LTPERTTALD LPQMVT.... ..HNADPRGT 101                                                                  150
E. coli    GFTVTIEAAE .GVTTGVSAA DRITTVRAAI ADGAKPSDLN RPGHVFPLRA
V. harv.   AFTVSIEAKE .GVTTGVSAK DRVTTVKTAT YFDAQPEDLA RPGHVFPLVA
S. cere.   AYTITVDVAQ .GTTTGISAH DRSMTCRALA DSSSTPKSFL KPGHICPLRA
A. goss.   AYTITCDYAH .GTTTGISAR DRALTVNQLA NPESKATDFT KPGHIVPLRA
M. gris.   AYTVSVDAEH PSTTTGISAH DRALACRMLA APDAQPSHFR RPGHVFPLRA 151                                                                  200
E. coli    QAGGVLTRGG HTEATIDLMT LAGFKPAGVL CELTNDD... ........GT
V. harv.   KTNGVLARRG HTEGTIDLMY LANLVPSGIL CELTNPD... ........GT
S. cere.   ADGGVLQRRG HTEAGVDLCK LSGLSPVAVI GELVND.... .....DEQGT
A. goss.   RDGGVLERDG HTEAALDLCR LAGVPEVAAI CELVSE.... .....RDVGL
M. gris.   VAGGVRARRG HTEAGVELCR LAGKRPVAVI SEIVDDGQEV EGRAVRAAPG 201                                                                  248
E. coli    MARAPECIEF ANKHNMALVT IEDLVAYRQA HERKAS---- --------
V. harv.   MAKLPETIEF ARRHGMPVLT IEDIVDYRTG IDLRNEYKSG LVREVSWS
S. cere.   MMRLNDCQAF GKKHGIPLIS IEELAQYLKK ---------- --------
A. goss.   MMTLDECIEF SKKHGLALIT VHDLKAAVAA KQ*------- --------
M. gris.   MLRGDECVAF ARRWGLKVCT IEDMIAHVEK TEGKLETNGS G*------
```

```
               1                                                                      50
E. coli    -MNQTLLSSF  GTPFERVENA  LAALREGRGV  MVLDDEDREN  EGDMIFPAET
V. harv.   MSSTSLLDEF  GTPVQRVERA  IEALKNGLGV  LLMDDEDREN  EGDLIFSAQH
S. cere.   ----------  --MFTPIDQA  IEHFKQNKFV  IVMDDAGREN  EGDLICAAEN
A. goss.   ---------M  TSPCTDIGTA  IEQFKQNKMI  IVMDHISREN  EADLICAAAH
M. gris.   --MPSTDSIP  KSNFDAIPDV  IQAFKNGEFV  VVLDDPSREN  EADLIIAAES 51                                                                     100
E. coli    MTVEQMALTI  RHGSGIVCLC  ITEDRRKQLD  LPMMV.....  .ENNTSAYGT
V. harv.   LTEAQMALMI  REGSGIVCLC  LTEERANWLD  LPPMV.....  .KDNCSKNQT
S. cere.   VSTEQMAFLV  RHSSGYVCAP  MTNAIADKLD  LPLLRTGMKF  ESNDDDRHGT
A. goss.   MTAEQMAFMI  RYSSGYVCAP  MTNAIADKLD  LPLMNT.LKC  KAFSDDRHST
M. gris.   VTTEQMAFMV  RHSSGLICAP  LTPERTTALD  LPQMVT....  ..HNADPRGT 101                                                                    150
E. coli    GFTVTIEAAE  .GVTTGVSAA  DRITTVRAAI  ADGAKPSDLN  RPGHVFPLRA
V. harv.   AFTVSIEAKE  .GVTTGVSAK  DRVTTVKTAT  YFDAQPEDLA  RPGHVFPLVA
S. cere.   AYTITVDVAQ  .GTTTGISAH  DRSMTCRALA  DSSSTPKSFL  KPGHICPLRA
A. goss.   AYTITCDYAH  .GTTTGISAR  DRALTVNQLA  NPESKATDFT  KPGHIVPLRA
M. gris.   AYTVSVDAEH  PSTTTGISAH  DRALACRMLA  APDAQPSHFR  RPGHVFPLRA 151                                                                    200
E. coli    QAGGVLTRGG  HTEATIDLMT  LAGFKPAGVL  CELTNDD...  ........GT
V. harv.   KTNGVLARRG  HTEGTIDLMY  LANLVPSGIL  CELTNPD...  ........GT
S. cere.   ADGGVLQRRG  HTEAGVDLCK  LSGLSPVAVI  GELVND....  .....DEQGT
A. goss.   RDGGVLERDG  HTEAALDLCR  LAGVPEVAAI  CELVSE....  .....RDVGL
M. gris.   VAGGVRARRG  HTEAGVELCR  LAGKRPVAVI  SEIVDDGQEV  EGRAVRAAPG 201                                             248
E. coli    MARAPECIEF  ANKHNMALVT  IEDLVAYRQA  HERKAS~~~~  ~~~~~~~~
V. harv.   MAKLPETIEF  ARRHGMPVLT  IEDIVDYRTG  IDLRNEYKSG  LVREVSWS
S. cere.   MMRLNDCQAF  GKKHGIPLIS  IEELAQYLKK  ~~~~~~~~~~  ~~~~~~~~
A. goss.   MMTLDECIEF  SKKHGLALIT  VHDLKAAVAA  KQ*~~~~~~~  ~~~~~~~~
M. gris.   MLRGDECVAF  ARRWGLKVCT  IEDMIAHVEK  TEGKLETNGS  G*~~~~~~
```

FIG. 1

3,4-DIHYDROXY-2-BUTANONE 4-PHOSPHATE SYNTHASE

FIELD OF THE INVENTION

This invention is in the field of fungal molecular biology. More specifically, this invention pertains to a nucleic acid fragment encoding a protein involved in the riboflavin biosynthetic pathway of fungi.

BACKGROUND OF THE INVENTION

Riboflavin, also referred to as vitamin $B_2$, is the precursor of flavin mononucleotide (FMN) and flavin adenine dinucleotide (FAD), essential cofactors for a number of mainstream metabolic enzymes that mediate hydride, oxygen, and electron transfer reactions. Riboflavin-dependent enzymes include succinate dehydrogenase, NADH dehydrogenase, ferredoxin-$NADP^+$ oxidoreductase, acyl-CoA dehydrogenase, and the pyruvate dehydrogenase complex. Consequently, fatty acid oxidation, the TCA cycle, mitochondrial electron-transport, photosynthesis, and numerous other cellular processes are critically dependent on either FMN or FAD as prosthetic groups. Other notable flavoproteins include glutathione reductase, glycolate oxidase, P450 oxido-reductase, squalene epoxidase, dihydroorotate dehydrogenase, and a-glycerophosphate dehydrogenase. Genetic disruption of riboflavin biosynthesis in *Escherichia coli* (Richter et al., *J. Bacteriol.* 174:4050–4056 (1992)) and *Saccharomyces cerevisiae* (Santos et al., *J. Biol. Chem.* 270:437444 (1995)) results in a lethal phenotype that is only overcome by riboflavin supplementation. This is not surprising, considering the ensemble of deleterious pleiotropic effects that would occur with riboflavin deprivation.

Riboflavin is synthesized by plants and numerous microorganisms, including bacteria and fungi (Bacher, A., *Chemistry and Biochemistry of Flavoproteins* (Müller, F., ed.) vol. 1, pp. 215–259, Chemical Rubber Co., Boca Raton, Fla. (1991)). Since birds, mammals, and other higher organisms are unable to synthesize the vitamin and, instead, rely on its dietary ingestion to meet their metabolic needs, the enzymes that are responsible for riboflavin biosynthesis are favorable targets for future antibiotics, fungicides, and herbicides as they should have no adverse affects on such nontarget organisms. Moreover, it is possible that the distantly-related plant and microbial enzymes have distinct characteristics that could be exploited in the development of potent organism-specific inhibitors. Thus, a detailed understanding of the structure, mechanism, kinetics, and substrate-binding properties of the riboflavin biosynthetic enzyme(s), from plants for example, would serve as a starting point for the rational design of chemical compounds that might be useful as herbicides. Having the authentic fungal or plant protein(s) in hand would also provide a valuable tool for the in vitro screening of chemical libraries in search of riboflavin biosynthesis inhibitors.

Fungal and bacterial riboflavin biosynthesis has been intensively studied for more than four decades (For recent reviews, see Bacher, A., *Chemistry and Biochemistry of flavoproteins* (Muller, F., ed.) vol. 1, pp. 215–259 and 293–316, Chemical Rubber Co., Boca Raton, Fla. (1990)). The synthetic pathway consists of seven distinct enzyme catalyzed reactions, with guanosine 5'-triphosphate (GTP) being the foremost precursor.

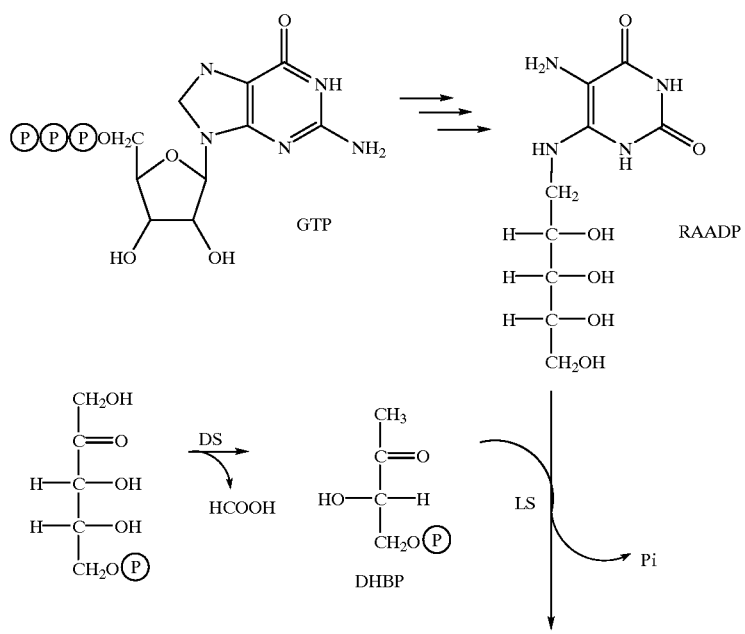

-continued

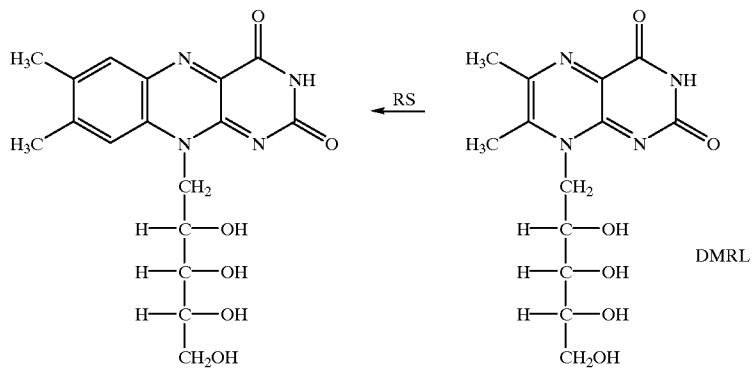

DMRL

While the second and third steps of riboflavin biosynthesis occur in opposite order in bacteria and fungi, the remaining pathway intermediates are identical in both microorganisms. Lumazine synthase (LS), the penultimate enzyme of riboflavin biosynthesis, catalyzes the condensation of 3,4-dihydroxy-2-butanone 4-phosphate (DHBP) with 4-ribitylamino-5-amino-2,6-dihydroxypyrimidine (RAADP) to yield 1 mol each of orthophosphate and 6,7-dimethyl-8-(1'-D-ribityl)-lumazine (DMRL), the immediate precursor of riboflavin. The terminal step of riboflavin biosynthesis is mediated by riboflavin synthase (RS). This enzyme catalyzes the dismutation of two molecules of MRL to yield 1 mol of riboflavin and RAADP.

Ribulose 5-phosphate serves as substrate for the formation of DHBP catalyzed by the enzyme 3,4-dihydroxy-2-butanone 4-phosphate synthase (DS). The complex enzyme reaction involving DS entails the elimination of C-4 from Ribulose 5-phosphate as formate via an intramolecular rearrangement as well as the conversion of the position 1 hydroxymethyl group to a methyl group. The catalytic process probably involves a sequence of tautomerization reactions. It is remarkable that such a complex reaction can be performed by a single and relatively small protein!

DS-encoding genes have been cloned from numerous organisms, including *Escherichia coli* (GenBank accession number X66720; Richter et al., *J. Bacteriol.* 174:40504056 (1992)), *Vibrio harvey* (GenBank accession number M27139; Swartztan et al., *J. Biol. Chem.* 265:3513–3517 (1989)), *Photobacterium phosphoreum* (GenBank accession number L11391; Lee et al., *J. Bacteriol.* 176:2100–2104 (1994)), *Bacillus substilis* (GenBank accession number X51510; Kil et al., *Mol. Gen. Genet.* 233:483–486 (1992)), *Bacillus amyloliquefaciens* (GenBank accession number X95955; Gusarov et al., *Mol. Biol.* 31:370–376 (1997)), *Actinobacillus pleuropneumoniae* (GenBank accession number U27202; Fuller et al., *J. Bacteriol.* 177:7265–7270 (1995)), *Saccharomyces cerevisiae* (GenBank accession number Z21619; Revuelta, J. L., direct submission; WO 9411515) and *Ashbya gossypii* (DGene accession number 95N-T03516; DE 4420785). While the various DS homologs all share certain structural features in common, their overall homology at the primary amino acid level is rather poor. For example, as determined with the Genetics Computer Group Gap program (Wisconsin Package Version 9.0, Genetics Computer Group (GCG), Madison, Wis. using their standard default values for "gap creation penalty" of 12 and "gap extension penalty" of 4), the *Escherichia coli* is only 61%, 25%, 16%, 27%, 33%, 45% and 43% identical to the homologous proteins of *Vibrio harveyi, Photobacterium phosphoreum, Bacillus substilis, Bacillus amyloliquefaciens, Actinobacillus pleuropneumoniae, Saccharomyces cerevisiae* and *Ashbya gossypii*, respectively. In addition, pairwise comparisons of these eight proteins reveal that the two most similar homologs share only 61% identity. The only known isolated fungal DS genes are that of *Ashbya gossypii* and *Saccharomyces cerevisiae*.

From the foregoing discussion, it is apparent that too little is known about fungal DS genes/proteins and their relationship to known microbial homologs to allow isolation of DS-encoding genes from any fungal or plant species using most classical approaches. The latter include hybridization probing of cDNA libraries with homologous or heterologous genes, PCR-amplification of the gene of interest using oligionucleotide primers corresponding to conserved amino acid sequence motifs, and/or immunological detection of expressed cDNA inserts in microbial hosts. Unfortunately, these techniques would not be expected to be very useful for the isolation of fungal or plant DS genes, since they all heavily rely on the presence of significant structural similarity (i.e., DNA or amino acid sequence) with known proteins and genes that have the same function. Given the observation that DS proteins are so poorly conserved, even amongst microorganisms, it is highly unlikely that the known microbial homologs would share significant structural similarities with their counterparts in higher plants.

An alternative approach that has been used to clone biosynthetic genes in other metabolic pathways from higher eucaryotes is through complementation of microbial mutants that are deficient in the enzyme activity of interest. Since this strategy relies only on the functional similarity between the disrupted host protein and the target gene of interest, it is ideally suited for cloning structurally dissimilar proteins that catalyze the same reaction. For functional complementation, a cDNA library is constructed in a vector that can direct the expression of the cDNA in the microbial host. The plasmid library is then introduced into the mutant microbe, and colonies are selected that are no longer phenotypically mutant. Indeed, the arabidopsis GTP cyclohydrolase II (Kobayashi et al, *Gene* 160:303–304 (1995)), LS (García-Ramírez et al., *J. Biol. Chem.* 270:23801–23807 (1995)) and RS (Santos et al., *J. Biol. Chem.* 270:437444 (1995)) of yeast, were all cloned through functional complementation of microbial riboflavin auxotrophs. This strategy has also worked for isolating genes from higher eucaryotes that are involved in other metabolic pathways, including lysine biosynthesis (Frisch et al., *Mol. Gen. Genet.* 228:287–293 (1991)), purine biosynthesis (Aimi et al., *J. Biol. Chem.* 265:9011–9014 (1990)), and tryptophan biosynthesis (Niyogi et al., *Plant Cell* 5:1011–1027 (1993)), and has also been successfully employed in the isolation of various plant genes including glutamine synthetase (Snustad et al., *Genetics* 120:1111–1124 (1988)), pyrroline-5-carboxylate reductase (Delauney et al., *Mol. Genet.* 221:299–305 (1990)), dihydrodipicolinate synthase (Frisch et al., *Mol. Gen. Genet.* 228:287–293 (1991)), 3-isopropylmalate dehydrogenase (Ellerstrom et al., *Plant Mol. Biol.* 18:557–566 (1992)), and dihydroorotate dehydrogenase (Minet et al., *Plant J.* 2:417422 (1992)).

Despite the obvious attractive features of cloning by functional complementation, there are several reasons why this approach might not work when applied to a fungal DS gene. First, the fungal cDNA sequence might not be expressed at adequate levels in the mutant microbe for a variety of reasons, including differences in preferred codon usage. Second, the cloned DS gene might not produce a functional polypeptide, if for instance, enzyme activity requires a post-translational modification, such as acetylation, glycosylation, or phosphorylation that is not carried out by the microbial host. Third, the heterologous fungal protein might be lethal to the host, thus rendering its expression impossible. Fourth, the fungal protein might fail to achieve its native conformation in the foreign microbial environment, due to folding problems, inclusion body formation, or various other reasons. If any of these events were to occur, cloning the DS gene by functional complementation would not be possible.

SUMMARY OF THE INVENTION

The instant invention relates to an isolated nucleic acid fragment encoding an indespensible fungal enzyme involved in riboflavin biosynthesis. Specifically, this invention concerns an isolated nucleic acid fragment encoding a fungal DS, wherein the fungus is *Magnaporthe grisea*. In addition, this invention relates to nucleic acid fragments that are complementary to a nucleic acid fragment encoding a fungal DS enzyme.

In another embodiment, the instant invention relates to chimeric genes encoding a fungal DS enzyme or to chimeric genes that comprise nucleic acid fragments that are complementary to the nucleic acid fragment encoding the enzyme, operably linked to suitable regulatory sequences, wherein expression of the chimeric genes results in production of levels of the encoded enzymes in transformed host cells that are altered (i.e., increased or decreased) from the levels produced in the untransformed host cells.

In a further embodiment, the instant invention concerns a transformed host cell comprising in its genome a chimeric gene encoding a fungal DS enzyme, operably linked to suitable regulatory sequences, wherein expression of the chimeric gene results in production of altered levels of a fungal DS enzyme in the transformed host cell. The transformed host cells can be of eucaryotic or procaryotic origin, and include cells derived from higher plants or microorganisms. The invention also includes transformed plants that arise from transformed host cells of higher plants, and from seeds derived from such transformed plants.

An additional embodiment of the instant invention, concerns a method of altering the level of expression of a fungal DS enzyme in a transformed host cell comprising: a) transforming a host cell with the chimeric gene encoding a fungal DS enzyme, operably linked to suitable regulatory sequences; and b) growing the transformed host cell under conditions that are suitable for expression of the chimeric gene wherein expression of the chimeric gene results in production of altered levels of DS in the transformed cell.

An additional embodiment of the instant invention concerns a method for obtaining a nucleic acid fragment encoding all or substantially all of an amino acid sequence encoding a fungal DS.

Additionally, a method is provided for evaluating at least one compound for its ability to inhibit the activity of a fungal DS enzyme and thus serve as a crop protection chemical comprising the steps of: (a) transforming a host cell with a chimeric gene comprising an isolated nucleic acid fragment encoding a fungal DS enzyme, the chimeric gene operably linked to suitable regulatory sequences; (b) growing the transformed host cell of step (a) under conditions suitable for expression of the chimeric gene wherein the expression of the chimeric gene results in the production of the fungal DS enzyme; (c) contacting the transformed host cell with a chemical compound; and (d) comparing the metabolic activity of the transformed host cell that has been contacted with the chemical compound with the metabolic activity of an untreated host cell, a decrease in metabolic activity in the contacted transformed host cell as compared to the untreated transformed host cell in step (d) indicating that the chemical compound is potentially useful as a crop protection chemical.

In an alternate embodiment, a method is provided for evaluating at least one compound for its ability to inhibit the activity of a fungal DS enzyme and thus serve as a crop protection chemical comprising the steps of: (a) transforming a host cell with a chimeric gene comprising a nucleic acid fragment encoding a fungal DS enzyme, the chimeric gene operably linked to suitable regulatory sequences; (b) growing the transformed host cell of step (a) under conditions suitable for expression of the chimeric gene wherein the expression of the chimeric gene results in the production of the fungal DS enzyme; (c) optionally purifying the enzyme expressed by the transformed host cell; (d) contacting the enzyme with a chemical compound; and (e) comparing the activity of the enzyme that has been contacted with the test compound to the activity of the untreated enzyme, a decrease in activity of the contacted enzyme as compared to the activity level of the untreated enzyme in step (e) indicating that the chemical compound is potentially useful as a crop protection chemical.

BRIEF DESCRIPTION OF THE DRAWINGS AND SEQUENCE DESCRIPTIONS

FIG. 1 shows a primary amino acid sequence alignment of known microbial DS homologs and the cloned *Magnaporthe grisea* DS protein that was generated with the GCG Pileup program (Genetics Computer Group, Madison, Wis.).

The following sequence descriptions and sequence listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are herein incorporated by reference. The present invention utilized Wisconsin Package Version 9.0 software from Genetics Computer Group (GCG), Madison, Wis. using their standard default values for "gap creation penalty" of 12 and "gap extension penalty" of 4. Gap uses the algorithm of Needleman and Wunsch to find the alignment of two complete sequences that maximizes the number of matches and minimizes the number of gaps.

SEQ ID NO:1 is the nucleotide sequence of a cloned cDNA encoding *Magnaporthe grisea* DS.

SEQ ID NO:2 is the deduced amino acid sequence of the cloned cDNA encoding *Magnaporthe grisea* DS.

SEQ ID NO:3 is the 5' primer useful in the amplification of *E. coli* DS having GenBank accession number X66720.

SEQ ID NO:4 is the 3' primer useful in the amplification of *E. coli* DS having GenBank accession number X66720.

SEQ ID NO:5 is the 5' primer useful for the introduction of a DNA fragment that confers kanamycin resistance into the *E. coli* DS gene having GenBank accession number X66720, respectively, at a NotI cleavage site.

SEQ ID NO:6 is the 3' primer useful for the introduction of a DNA fragment that confers kanamycin resistance into the *E. coli* DS gene having GenBank accession number X66720, respectively, at a NotI cleavage site.

SEQ ID NO:7 is one of the PCR primers useful for the introduction of a NotI cleavage site in the middle of *E. coli* DS having GenBank accession number X66720. (hybridizes to nt 968–987).

SEQ ID NO:8 is one of the PCR primers useful for the introduction of a NotI cleavage site in the middle of *E. coli* DS having GenBank accession number X66720. (hybridizes to nt 940–957).

SEQ ID NO:9 is the 5' primer useful for introducing *Magnaporthe grisea* DS into the *E. coli* expression vector, pET-24a (+) (Novagen).

SEQ ID NO:10 is the 3' primer useful for introducing *Magnaporthe grisea* DS into the *E. coli* expression vector, pET-24a (+) (Novagen).

DETAILED DESCRIPTION OF THE INVENTION 3,4-Dihydroxy-2-butanone 4-phosphate synthase (DS) of the *Magnaporthe grisea* riboflavin biosynthetic pathway has been cloned by functional complementation of an *Escherichia coli* auxotroph.

A nucleic acid fragment that encodes the DS protein has been isolated from *Magnaporthe grisea*. The invention also includes an assay using the protein that is encoded for by the nucleic acid fragment to screen for crop protection chemicals (e.g., fungicides) related to the fungal riboflavin biosynthetic pathway.

In this disclosure, a number of terms and abbreviations are used. The following definitions are provided.

"3,4-Dihydroxy-2-butanone 4-phosphate synthase" is abbreviated as DS, and refers to the enzyme that catalyzes the conversion of ribulose 5-phosphate to 3,4-dihydroxy-2-butanone 4-phosphate and formic acid.

"Polymerase chain reaction" is abbreviated PCR.

"Expressed sequence tag" is abbreviated EST.

"3,4-Dihydroxy-2-butanone 4-phosphate" is abbreviated DHBP.

"Isopropyl-1-thio-β-D-galactopyranoside" is abbreviated IPTG.

"Sodium dodecylsulfate-polyacrylamide gel electrophoresis" is abbreviated SDS-PAGE.

"Open reading frame" is abbreviated ORF.

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Auxotrophy" refers to the nutritional requirements necessary for growth, sporulation and crystal production of the microorganism. For the purpose of this invention, the term "auxotroph" is defined herein to mean an organism which requires the addition of riboflavin for growth.

The terms "host cell" and "host organism" refer to a cell capable of receiving foreign or heterologous genes and expressing those genes to produce an active gene product. Suitable host cells include microorganisms such as bacteria and fungi, as well as plant cells.

The term "metabolic activity" refers to the normal cellular activity needed to support growth. As used herein agents, such as crop protection chemicals, that will inhibit metabolic activity will generally inhibit cell growth.

The term, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol. 215:403–410* (1990); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides (generally 12 bases or longer) may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

For example, it is well known in the art that antisense suppression and co-suppression of gene expression may be accomplished using nucleic acid fragments representing less than the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product.

Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein.

"Codon degeneracy" refers to redundancy in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the DS biosynthetic enzyme as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=and gap extension penalty=4 (Devereux et al., *Nucleic Acids Res.* 12:387–395 (1984)), BLASTP, BLASTN, and FASTA (Pearson et al., *Proc. Natl. Acad. Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "complementary" is used to describe the relationship between nucleotide bases that are capable of hybridizing to one another. Hence with respect to DNA, adenosine is complementary to thymine and cytosine is complementary to guanine.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochemistry of Plants* 15:1–82 (1989)). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed MRNA upstream of the translation start sequence. The translation leader sequence may affect processing of the primary transcript to mRNA, MRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include polyadenylation recognition sequences and other sequences encoding regulatory signals capable of affecting MRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (MRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or MRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of MRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth. Enzymol.* 143:277 (1987)) and particle-accelerated or "gene gun" transformation technology (Klein et al., *Nature, London* 327:70–73 (1987); US 4,945,050).

A *Magnaporthe grisea* DS has been isolated and identified by comparison of random cDNA sequences to the GenBank database using the BLAST algorithms well known to those skilled in the art. The nucleotide sequence of *Magnaporthe grisea* DS cDNA is provided in SEQ ID NO:1, and the deduced amino acid sequence is provided in SEQ ID NO:2. A DS gene from other fungi can now be identified by comparison of random cDNA sequences to the *Magnaporthe grisea* DS sequence provided herein.

The nucleic acid fragment of the instant invention may be used to isolate cDNAs and genes encoding a homologous DS from the same or other fungal species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR) or ligase chain reaction).

For example, DS genes, either as cDNAs or genomic DNAs, could be isolated directly by using all or a portion of the instant nucleic acid fragments as DNA hybridization probes to screen libraries from any desired fungus employing methodology well known to those skilled in the art. Specific oligonucleotide probes based upon the instant DS sequence can be designed and synthesized by methods known in the art (Maniatis infra). Moreover, the entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragment may be used in PCR protocols to amplify longer nucleic acid fragments encoding homologous DS genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the MRNA precursor encoding fungal DS. Alternatively, the second primer sequence may be based upon sequences derived from the cloning vector. For example, the skilled artisan can follow the RACE protocol (Frohman et al., *Proc. Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Finally, availability of the instant nucleotide and deduced amino acid sequence facilitates immunological screening cDNA expression libraries. Synthetic peptides representing portions of the instant amino acid sequence may be synthesized. These peptides can be used to immunize animals to produce polyclonal or monoclonal antibodies with specificity for peptides or proteins comprising the amino acid sequence. These antibodies can be then be used to screen cDNA expression libraries to isolate full-length cDNA clones of interest (Lerner et al., *Adv. Immunol.* 36:1 (1984); Maniatis infra).

The nucleic acid fragments of the instant invention may also be used to create transgenic plants in which the instant DS protein is present at higher or lower levels than normal. Such manipulations would conceivably alter the intracellular levels of riboflavin, hence the essential cofactors FAD and FMN, producing novel phenotypes of potential commercial value. Alternatively, in some applications, it might be desirable to express the instant DS protein in specific plant tissues and/or cell types, or during developmental stages in which they would normally not be encountered.

Overexpression of the instant DS may be accomplished by first constructing a chimeric gene in which the DS coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The instant chimeric genes may also comprise one or more introns in order to facilitate gene expression.

Plasmid vectors comprising the instant chimeric genes can then be constructed. The choice of a plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida etal., *Mol. Gen. Genetics* 218:78–86 (1989)), and thus that multiple events must be screened in order to obtain lines displaying the desired expression level and pattern. Such screening may be accomplished by Southern analysis of DNA, Northern analysis of MRNA expression, Western analysis of protein expression, or phenotypic analysis.

For some applications it may be useful to direct the DS protein to different cellular compartments or to facilitate their secretion from the cell. It is thus envisioned that the chimeric gene described above may be further modified by the addition of appropriate intracellular or extracellular targeting sequence to their coding regions. These include chloroplast transit peptides (Keegstra et al., *Cell* 56:247–253 (1989), signal sequences that direct proteins to the endoplasmic reticulum (Chrispeels et al., *Ann. Rev. Plant Phys.*

*Plant Mol.* 42:21–53 (1991), and nuclear localization signal (Raikhel et al., *Plant Phys.* 100:1627–1632 (1992). While the references cited give examples of each of these, the list is not exhaustive and more targeting signals of utility may be discovered in the future. It has been shown, for example, that the mature spinach RS is localized in chloroplasts. It has been further demonstrated that antibodies directed against the purified recombinant protein specifically interact with a polypeptide of the expected size when spinach chloroplast extracts are subjected to SDS-PAGE and Western analysis.

It may also be desirable to reduce or eliminate expression of the DS gene in plants for some applications. In order to accomplish this, chimeric gene designed for antisense or co-suppression of DS can be constructed by linking the genes or gene fragments encoding parts of these enzymes to plant promoter sequences. Thus, a chimeric gene designed to express antisense RNA for all or part of DS can be constructed by linking the DS gene or gene fragments in reverse orientation to plant promoter sequences. The co-suppression or antisense chimeric gene constructs could then be introduced into plants via well known transformation protocols to reduce or eliminate the endogenous expression of DS gene products.

The DS protein produced in heterologous host cells, particularly in the cells of microbial hosts, can be used to prepare antibodies to the enzymes by methods well known to those skilled in the art. The antibodies would be useful for detecting the instant DS protein in situ in cells or in vitro in cell extracts. Preferred heterologous host cells for production of the instant DS protein are microbial hosts. Microbial expression systems and expression vectors containing regulatory sequences that direct high level expression of foreign proteins are well known to those skilled in the art. Any of these could be used to construct chimeric genes for production of the instant DS. These chimeric genes could then be introduced into appropriate microorganisms via transformation to provide high level expression of the instant DS protein.

Microbial host cells suitable for the expression of the instant DS enzymes include any cell capable of expression of the chimeric genes encoding these enzymes. Such cells will include both bacteria and fungi including, for example, the yeasts (e.g., Aspergillus, Saccharomyces, Pichia, Candida, and Hansenula), members of the genus Bacillus as well as the enteric bacteria (e.g., Escherichia, Salmonella, and Shigella). Methods for the transformation of such hosts and the expression of foreign proteins are well known in the art and examples of suitable protocols may be found in *Manual of Methods for General Bacteriology* (Gerhardt et al., eds., American Society for Microbiology, Washington, DC. (1994) or in Brock, T. D., *Biotechnology: A Textbook of Industrial Microbiology*, Second Edition, Sinauer Associates, Inc., Sunderland, Mass. (1989)).

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, which are useful to drive expression of the gene encoding the DS enzyme in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $lP_L$, $lP_R$, T7, tac, and trc (useful for expression in *Escherichia coli*). Termination control regions may also be derived from various genes native to the preferred hosts. Optionally, a termination site may be unnecessary, however, it is most preferred if included.

The instant DS protein can also be used as a tool to facilitate the design and/or identification of specific chemical agents that might prove useful as fungicides, herbicides, or antibiotics. This could be achieved either through the rational design and synthesis of potent enzyme inhibitors that result from structural and/or mechanistic information that is derived from the purified instant fungal protein, or through random in vitro screening of chemical libraries. The DS protein catalyzes an indispensable step in the synthesis of riboflavin in plants and most microorganisms, and is required for the production of FAD and FMN, essential prosthetic groups for a number of important redox enzymes. Consequently, it is anticipated that significant in vivo inhibition of any DS protein will severely cripple cellular metabolism and will likely result in the death of any organism that requires the endogenous production of riboflavin as its only source of the vitamin.

All or a portion of the nucleic acid fragments of the instant invention may also be used as probes for genetically and physically mapping the genes that they are a part of, and as markers for traits linked to expression of the instant DS. Such information may be useful in plant breeding in order to develop lines with desired phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., *Am. J. Hum. Genet.* 32:314–331 (1980)).

The production and use of plant gene-derived probes for use in genetic mapping is described by Bernatzky and Tanksley (*Plant Mol. Biol. Reporter* 4:37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., *Nonmammalian Genomic Analysis: A Practical Guide*, pp. 319–346, Academic Press (1996), and references cited therein).

In another embodiment, nucleic acid probes derived from the instant nucleic acid sequence may be used in direct fluorescence in situ hybridization (FISH) mapping. Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequences. This, however, is generally not necessary for mapping methods. Such information may be useful in plant breeding in order to develop lines with desired phenotypes.

EXAMPLES

The present invention is farther defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard recombinant DNA and molecular cloning techniques used here are well known in the art and are described by Sambrook, J., Fritsch, E. F. and Maniatis, T. *Molecular Cloning: A Laboratory Manual*, Cold Spring Harbor Laboratory Press, Cold Spring Harbor, 1989; and by T. J. Silhavy, M. L. Bennan, and L. W. Enquist, *Experiments with Gene Fusions*, Cold Spring Harbor Laboratory Cold Press Spring Harbor, N.Y. (1984) and by Ausubel, F. M. et al., *Current Protocols in Molecular Biology*, published by Greene Publishing Assoc. and Wiley-Interscience (1987).

Manipulations of genetic sequences were accomplished using the suite of programs available from the Genetics Computer Group Inc. (Wisconsin Package Version 9.0, Genetics Computer Group (GCG), Madison, Wis.).

The meaning of abbreviations is as follows: "sec" means second(s), "min" means minute(s), "h" means hour(s), "d" means day(s), "EL" means microliter, "mL" means milliliters, "L" means liters, "mM" means millimolar, "M" means molar, "mmol" means millimole(s).

Example 1

PCR-Cloning of *Escherichia coli* DS

Gene specific PCR primers were used to amplify the *Escherichia coli* DS gene from genomic DNA, while adding unique restriction sites to its flanking regions for subsequent ligation into high copy number plasmids. The primers used for this purpose were based on the published DNA sequences of the *Escherichia coli* DS gene (GenBank accession number X66720) and consisted of the following nucleotides:

Primer 1—(SEQ ID NO:3):
   5'-ACT CAT TTA cca tgg C TC AGA CGC TAC TTT CCT C-3'

Primer 2—(SEQ ID NO:4):
   5'-ATC TTA CTg tcg ac T TCA GCT GGC TTT ACG CTC-3'

The underlined bases hybridize to the target gene, while lower case letters indicate the restriction sites (NcoI or SalI) that were added to the ends of the PCR primers.

Amplifiication of the DS gene was achieved using Primers 1 and 2, and genomic DNA from *Escherichia coli* strain W3110 (Campbell et al., *Proc. Natl. Acad. Sci.* 75:2276–2284 (1978)). Primer 1 hybridizes at the start of the gene and introduces a NcoI site at the protein's initiation codon, while Primer 2 hybridizes at the opposite end and provides a SalI site just past the termination codon. The 100-$\mu$L PCR reactions contained ~100 ng of genomic DNA and both primers at a final concentration of 0.5 $\mu$M. The other reaction components were provided by the GeneAmp PCR Reagent Kit (Perkin Elmer), according to the manufacturer's protocol. Amplification was carried out in a DNA Thermocycler 480 (Perkin Elmer) for 28 cycles, each comprising 1 min at 94° C., 2 min at 53° C., and 2 min at 72° C. Following the last cycle, there was a 7-min extension period at 72° C. The PCR product was cut with NcoI and SalI, and ligated into similarly digested pGEM-5Zf (+) (Promega, Madison, Wis.). The latter was chosen as a suitable cloning vector since it lacks a NotI cleavage site after double-digestion with NcoI and SalI (see below). The ligation reaction mixture was used to transform *Escherichia coli* DH5α competant cells (GibcoBRL), and transformants were selected on LB media supplemented with 100 $\mu$g/mL ampicillin.

Plasmids harboring the cloned *Escherichia coli* DS gene were identified by restriction digestion analysis. Plasmid DNA was isolated from a number of ampicillin-resistant colonies using the Wizard DNA Purification System (Promega, Madison, Wis.) and subjected to cleavage with NcoI and SalI. The samples were analyzed by agarose gel electrophoresis, and a representative plasmid for the gene, yielding an insert of the correct size, was sequenced completely to verify the absence of PCR errors. Apart from those nucleotides at the 5' and 3' ends that were intentionally altered for cloning purposes, the amplified *Escherichia coli* DS gene sequence was identical to that reported in the literature.

Example 2

Insertional Inactivation of the *Escherichia coli* DS Gene

In order to create bacterial auxotrophs lacking the ability to synthesize riboflavin, the cloned *Escherichia coli* DS gene was rendered nonfunctional through insertional inactivation. Briefly, a unique NotI site was introduced in the middle of the coding region of the target genes, and a DNA fragment that confers kanamycin resistance was ligated into the engineered site. The latter was provided by the commercially available Kan$^r$ GenBlock cartridge (Pharmacia), that was modified through PCR to add NotI cleavage sites at both of its ends. This modification was accomplished using Primers 3 and 4 in a standard PCR reaction; the underlined portions hybridize to the Kan$^r$ GenBlock, and lower case letters indicate the NotI cleavage sites.

Primer 3—(SEQ ID NO:5):

5'-AAC TAG ATC Agc ggc cgc AGC CAC GTT GTG TCT CAA A-3'

Primer 4—(SEQ ID NO:6):

5'-GAC AAA CAT Agc ggc cgc TGA GGT CTG CCT CGT GAA-3'

Following amplification, the modified Kanr GenBlock was cleaved with NotI, and the resulting fragment was purified by agarose gel electrophoresis.

PCR primers were also used to introduce a unique NotI cleavage site in the middle of the Escherichia coli DS gene. This was accomplished through an application of the "inverse PCR" technique that is fully described by Ochman, et al. in PCR Protocols: A Guide to Methods and Applications, (Innis et al., eds.) pp. 219–227, Academic Press, San Diego, Calif., (1990). The targets for inverse PCR are usually double-stranded circular DNA molecules. However, in contrast to other PCR applications, the two primers are oriented away from each other such that their 3' ends are extended in opposite directions around the entire circular template. If the primers are designed to hybridize immediately adjacent to each other, a linear DNA fragment is produced that includes the entire vector sequence and has as its starting and stopping points the original primer binding sites. The net result is analogous to linearizing a circular plasmid at a specified location. By attaching appropriate nucleotide sequences to the non-hybridizing 5' ends of both PCR primers, it is therefore possible to introduce a unique restriction site at any desired location within a circular template.

Primers 5 and 6 (which hybridize to nt 968–987 and nt 940–957 of the DNA sequence in GenBank accession number X66720) were designed to introduce a NotI cleavage site in the middle of the Escherichia coli DS gene; the nucleotides that hybridize to the target gene are underlined, and NotI cleavage sites are indicated in lower case letters.

Primer 5—(SEQ ID NO:7):

5'-AAC TAG ATC Agc g gc cgc TGA CCG TAT TAC GAC-3'

Primer 6—LS (SEQ ID NO:8):

5'-GAC AAA CAT Agc ggc cgc GTA GTC ACA CCT TCA GCT-3'

The circular template for inverse PCR was the pGEM-5Zf (+) construct containing the Escherichia coli DS gene. The 100-µL PCR reactions contained 0.5 ng of plasmid DNA and Primer 5 and Primer 6, both at a final concentration of 0.5 µM. Amplification was carried out in a DNA Thermocycler 480 (Perkin Elmer) for 30 cycles, each comprising 50 sec at 94° C., 1 min at 55° C., and 3 min at 72° C. The PCR product was cleaved with NotI and the resulting fragment was purified by agarose gel electrophoresis; the excised band was of the expected size. Next, the purified fragment was recircularized with T4 DNA ligase (Novagen) to regenerate a functional plasmid, and an aliquot of the ligation reaction mixture was used to transform Escherichia coli DH5α competent cells (GibcoBRL). Growth was selected for on LB media containing ampicillin (100 µg/mL), and plasmid DNA was isolated from a number of transformants for restriction digestion analysis with NotI, SalI, and NcoI. A representative plasmid yielding the correct cleavage pattern with these enzymes was selected for further manipulation.

To insert the kanamycin resistance gene, the plasmid construct described above was cleaved with NotI and purified by agarose gel electrophoresis. The fragment was then incubated with a 4-fold molar excess of the modified Kan$^r$ GenBlock cartridge, and subjected to a standard ligation reaction in the presence of T4 DNA ligase (Novagen). An aliquot of the ligation reaction mixtures was used to transform Escherichia coli DH5α competent cells (GibcoBRL), and growth was selected for on LB plates containing kanamycin (30 µg/mL) and ampicillin (100 µg/mL). Plasmids harboring the disrupted Escherichia coli DS gene were identified by restriction digestion analysis. The plasmids were cleaved with NcoI and SalI, and were then subjected to agarose gel electrophoresis to check for the presence of the inserted kanamycin resistance gene. A representative plasmid, yielding fragments of the correct size, was selected for further manipulation. DNA sequence analysis of this plasmid confirmed that the kanamycin resistance gene had been inserted at the correct location in the target gene.

Example 3

Generation of Escherichia coli DS Auxotroph

The insertionally inactivated Escherichia coli DS was liberated from the plasmid construct described above using NcoI and SalI and purified by agarose gel electrophoresis. The fragment was then introduced into Escherichia coli strain ATCC 47002 (fully described in Balbas et al., Gene 136:211–213 (1993), and isogenic with JC7623 (described by Bachmann, B., in Escherichia coli and Salmonella typhimurium: Cellular and Molecular Biology (Niedhardt et al., eds.) p. 2466, American Society of Microbiology, Washington, D.C. (1987)) by electroporatation using a BTX Transfector 100 (Biotechnologies and Experimental Research Inc.) according to the manufacturer's protocol. The choice of this strain as the initial recipient for gene replacement was based on its well established hyper-rec phenotype and related ability to undergo high frequency double-crossover homologous recombination (Wyman et al., Proc. Nat. Acad. Sci. USA 82:2880–2884 (1985); Balbas et al., Gene 136:211–213 (1993); Balbas et al., Gene 172:65–69 (1996)). Thus, it was anticipated that the insertionally inactivated Escherichia coli DS gene would efficiently replace its functional chromosomal counterpart in ATCC 47002 under kanamycin selection.

Following electroporation, the transformed cells were resuspended in 1.0mL of S.O.C. media (GibcoBRL) that was supplemented with riboflavin (400 µg/mL), and incubated for 1 h at 37° C. Kanamycin resistance was then selected for on LB plates at 37° C. that contained both riboflavin (400 µg/mL) and kanamycin (30 µg/mL); colonies appeared 24–48 h later. Phenotypic detection of the correct chromosomal integration event was accomplished through replica-plating experiments. Riboflavin auxotrophs resulting from double-crossover homologous recombination of the disrupted target gene would be expected to be resistant to kanamycin, sensitive to ampicillin, and to exhibit growth only in the presence of added riboflavin. A representative bacterial colony exhibiting this phenotype was selected for further study.

While ATCC 47002 is an excellent strain for creating Escherichia coli "knockouts", its multiple mutations in the recBCD loci render it incapable of propagating ColE1-type plasmids (Balbas et al., Gene 172:65–69 (1996)). Consequently, the riboflavin auxotroph described above is not suitable for screening plasmid cDNA libraries by functional complementation. In order to achieve this goal it was therefore necessary to move the insertionally inactivated DS gene from the chromosome of ATCC 47002 to a suitable wildtype background. This manipulation was accomplished through generalized phage transduction using P1$_{vir}$ and standard methodologies as fully described by Miller, J. H., in *Experiments in Molecular Genetics*, pp. 201–205, Cold Spring Harbor Laboratory, Cold Spring Harbor, New York, (1972). *Escherichia coli* W3110 (Campbell et al., *Proc. Nat.l Acad. Sci.* 75:2276–2284 (1978)) was selected as the recipient strain for the insertionally inactivated DS gene. Following phage transduction, bacterial growth was selected for on LB media that was supplemented with kanamycin (35 μg/mL) and riboflavin (400 μg/mL). Stable transductants harboring the disrupted *Escherichia coli* DS gene were then identified through replica-plating experiments analogous to those described above for ATCC 47002. Thus, individual colonies were patched onto plates containing LB media, sodium citrate (7.5 mM), magnesium sulfate (1.5 mM), and kanamyacin (35 μg/mL), with or without riboflavin (400 μg/mL). The DS riboflavin auxotroph that was selected for further study and subsequent complementation cloning (see below) was only able to grow in the presence of added riboflavin, and was not resistant to ampicillin (100 μg/mL) or streptomycin (25 μg/mL); sensitivity to streptomycin is characteristic of W3110, but not of ATCC 47002.

Example 4

Cloning of the *Magnaporthe grisea* DS Gene Through Functional Complementation

A *Magnaporthe grisea* cDNA expression library, in the NotI and SalI cleavage sites of the Lambda ZipLox vector (GibcoBRL), was prepared from isolated MRNA using conventional methodologies (Maniatis supra), and subjected to mass excision using the manufacturer's protocol. Upon excision, the liberated cDNA inserts are contained in the plasmid vector pZL1 which confers resistance to amipicillin, and allows their expression in *Escherichia coli* upon induction with isopropyl-1-thio-β-D-galactopyranoside (IPTG). The resulting mixture of excised plasmids was then electroporated into the *Escherichia coli* DS auxotroph (the W3110-derivative) using a BTX Transfector 100 (Biotechnologies and Experimental Research Inc.) and the manufacturer's protocol. The transformed cells were selected for growth in the absence of added riboflavin, on plates that contained B agar (LB media containing sodium citrate (7.5 mM), magnesium sulfate (1.5 mM), kanamyacin (35 $\mu$g/mL), ampicillin (100 $\mu$g/mL), and IPTG (0.6 mM)). Following a 48-hr incubation period at 37° C., bacterial growth was observed and riboflavin-independant colonies were recovered at frequencies of about $2.1\times10^{-5}$. Plasmid DNA was isolated from a representative colony and subjected to further analysis; the selected plasmid was able to transform the *Escherichia coli* DS auxotroph to riboflavin prototrophy at high frequency. The cDNA insert contained in this plasmid was then sequenced completely on an ABI 377 automated sequencer (Applied Biosystems), using fluorescent dideoxy terminators and custom-designed primers.

The approximately 1.3 kbp *Magnaporthe grisea* cDNA insert that rescued the *Escherichia coli* DS auxotroph clearly encodes a 3,4-dihydroxy-2-butanone 4-phosphate synthase. The nucleotide sequence of the open reading frame (ORF) for this protein and its predicted primary amino acid sequence are set forth in SEQ ID NO:1 and SEQ ID NO:2, respectively.

Of the various microbial DS homologs that are shown in FIG. 1, the *Mangaporthe grisea* protein (SEQ ID NO:2) show the greatest similarity to the *Vibrio harveyi* and *Saccharomyces cerevisiae* proteins at the primary amino acid sequence level (e.g., approximately 53% identity). Presently, the only known isolated fungal DS genes are that of *Ashbya gossypii* and *Saccharomyces cerevisiae*. Pairwise comparisons of the three fungal DS proteins affords the following percent identities:

52.5%—*Mangaporthe grisea* versus *Saccharomyces cerevisiae.*

48.1%—*Mangaporthe grisea* versus *Ashbya gossypii.*

59.9%—*Saccharomyces cerevisiae* versus *Ashbya gossypii.*

From the foregoing numbers, it is apparent the known fungal DS proteins have a rather poor overall homology at their primary amino acid level. In addition, the *Magnaporthe grisea* DS is approximately only 44% identical to the corresponding protein of *Eschericihia coli.*

Example 5

Expression of *Magnaporthe grisea* DS in *Escherichia coli*

The cloned *Magnaporthe grisea* DS, identified in Example 4, was modified for insertion into the T7 promoter-based *Escherichia coli* expression vector, pET-24a (+) (Novagen), using primers 7 (SEQ ID NO:9) and 8 (SEQ ID NO:10). Primer 7 (5'-CTA CTC ATT TCA TAT GCC TTC CAC AGA CAG CAT-3') (SEQ ID NO:9) hydridizes to nt 1–20 of the *Magnaporthe grisea* DS (SEQ ID NO:1). It was designed to initiate protein synthesis in *Escherichia coli* at the normal starting point and incorporates for cloning purposes a unique NdeI site upstream from the initiator Met residue. Primer 8 (5'-CAT CTT ACT AGA TCT TCA ACC CGA CCC ATT CGT C-3') (SEQ ID NO:10) hybridizes at the other end of the ORF to nt 684–702 and introduces a unique BglII site just past the protein's stop codon. The target for PCR amplification was the purified plasmid ontaining the cDNA insert for the *Magnaporthe grisea* DS. The predicted PCR product encodes the full-length *Magnaporthe grisea* DS with no modifications (SEQ ID NO:2).

Following amplification of the target gene, the PCR fragment was cleaved with NdeI and BglII, and ligated into the NdeI and BamHI sites of the polylinker region of pET-24a (+) (Novagen). The latter is a high-level *Escherichia coli* expression vector that contains a T7 promoter and is selected for on kanamycin. An aliquot of the ligation reaction mixture was then used to transform a plasmid-bearing derivative of *Escherichia coli* BL21(DE3) using a BTX Transfector 100 (Biotechnologies and Experimental Research Inc.) according to the manufacturer's protocol. The plasmid contained in the BL21(DE3) cells that were used for transformation was pGroESL (Goloubinoff et al., *Nature* 337:44–47 (1985)), which confers resistance to chloramphenicol and constitutively overexpresses the *Escherichia coli* GroEL and GroESproteins, two molecular chaperones that are known from previous studies to assist in the folding of certain other proteins. It was anticipated that the presence of pGroESL in the bacterial host cells would improve the production of soluble *Magnaporthe grisea* DS which otherwise is found exclusively in inclusion bodies. Following the transformation procedure, the cells were plated on LB media that contained both kanamyacin (50 $\mu$g/ml) and chloramphenicol (60 $\mu$g/mL), and incubated at 37° C. to obtain single colonies. Clones harboring a *Magnaporthe grisea* DS insert in pET-24a (+) were identified through PCR reactions using individual resuspended colonies and primers 7 and 8. Following this procedure, a representative clone was selected for the production of recombinant protein (see below) and its plasmid DNA was sequenced completely to check for PCR errors; none were found.

To express *Magnaporthe grisea* DS in *Escherichia coli* the strain described above was grown at 37° C. in LB media that contained kanamycin (50 μg/mL) and chloramphenicol (60 μg/mL). The cells were induced with IPTG (1 mM) at an $A_{600\ nm}$ of ~1.0, and harvested 3 h later by centrifugation. *Magnaporthe grisea* DS was well expressed in the bacterial host at levels exceeding 10% of the total protein. However, even with overexpression of GroEL and GroES, only about 25% of the recombinant protein was found to be soluble, and it was this material that was purifed as described below.

Example 6

Purification of Recombinant *Magnaporthe grisea* DS

Purification steps were performed at 04° C. *Escherichia coli* cell pellets containing (6.4 g wet wt.) *Magnaporthe grisea* DS were suspended in 3 volumes of 50 mM Tris-HCl, 2 MM $MgCl_2$, pH 7.5 (Buffer P). The suspension was disrupted in a French pressure cell at 20,000 psi with 3 passes though the cell with cooling on wet ice between each passage. The resulting homogenate was centrifuged 20 min at 18,500 g and 5 mL of the resulting supernatant (53 mg/mL) was loaded onto a Pharmacia Q-Sepharose Fast Flow column (1×5 cm) equilibrated with Buffer P. After washing the column with 15 mL of Buffer P, the column was developed with a linear gradient (0–1M NaCl in Buffer P). DS activity eluted towards the end of the gradient. Active fractions were pooled (200 mg protein in 10 mL), concentrated to 5 mL and diafiltered 50× against 5 mM potassium phosphate, 2.0 mM $MgCl_2$, pH 7.5 before loading onto a Calbiochem hydroxylapatite column (1×7 cm) equilibrated with 5 mM potassium phosphate, 2.0 mM $MgCl_2$, pH 7.5. Active fractions eluted in the column wash with equilibration buffer. They were concentrated to 2.5 mL (5.4 mg/mL) and diafiltered 20× against 50 mM Tris-HCl, pH 7.5 before flash freezing in liquid $N_2$ followed by storage at –80° C. until use. The purified DS was homogeneous as judged by SDS-PAGE and Coomassie blue staining. Yield of DS was 13.5 mg based on an extinction coefficient at 280 nm of 7270 $M^{-1}\ cm^{-1}$ as calculated through the GCG Peptidesort program (Genetics Computer Group, Madison, Wis.). Yield of DS activity (1.5 μmole/min) was 35% of that in the crude homogenate. Specific activity was 0.11 μmole/min/mg protein representing a 10-fold purification over the crude homogenate.

Edman degradation of purified recombinant *Magnaporthe grisea* DS revealed that its first 17 amino acids are identical to those of the protein shown in SEQ ID NO:2. However, like a number of other proteins that are overexpressed in *Escherichia coli*, its initiator Met residue is removed by the bacterial host.

Taking this into account, its predicted molecular mass is 24871.88 daltons, which is in excellent agreement with the value that was determined using electrospray ionization mass spectrometry (24870.7). More importantly, purified recombinant *Magnaporthe grisea* DS is catalytically active. In the in vitro enzyme assay described below, it exhibited a turnover number of approximately 2.8 $min^{-1}$ (based on protomer) at 25° C. By way of comparison, the reported turnover number for *Escherichia coli* DS at 37° C. is 0.66 $min^{-1}$ (Richter et al., *J. Bacteriol.* 174:4050–4056 (1992)) and *Candida guilliermondii* DS at 37° C. is 5.6 $min^{-1}$ (Volk et al., *J. Biol. Chem.* 265:19479–19485 (1990)). Assuming that the enzyme reaction is characterized by a Q10 (temperature coefficient) of 2, these observations suggest that the purified recombinant *Magnaporthe grisea* DS is probably fully active.

Example 7

Assay for Measuring DS Enzyme Activity

Assays (0.125 mL) for DS activity were conducted in 96 well plates at 25° C. Reactions (30 min) included 50 mM Tris-HCl, 10 mM $MgCl_2$, 5 mM riblse 5-phosphate, 0.25 unit of pentose phosphate isomerase and DS. Ribose 5-phosphate and pentose phosphate isomerase were used to generate DS substrate ribulose 5-phosphate in equilibrium with ribose 5-phosphate for economy and purity reasons. In practice, ribose 5-phosphate and pentose phosphate isomerase may be replaced with the genuine DS substrate, ribulose 5-phosphate, with very similar results. The implication is that ribose 5-phosphate does not interfere with the catalystic properties of DS. After 30 min, product 3,4-dihydroxy-2-butanone 4-phosphate was determined by a modification of a method which was developed for the determination of diacetyl (Mattessich et al. *Anal. Biochem.* 180:349–350 (1989)). To each reaction was added 0.1 mL of a saturated creatine solution followed by 0.05 mL of an a-naphthol solution (35 mg/mL in 1.0 N NaOH). Standard curves were established with 0–36 nmol/0.125 mL of diacetyl or 3,4-dihydroxy-2-butanone 4-phosphate and treating them as above for the reaction samples. Color was allowed to develop 30 min before reading absorbances at 525 nm by using a Spectra Max Plus plate reader (Molecular Devices). For inhibition assays, ribose 5-phosphate concentrations were changed to 0.5 mM and inhibitors were added to the reactions in 2 μL of DMSO.

What is claimed is:

1. An isolated nucleic acid fragment encoding a DS enzyme selected from the group consisting of:
   (a) an isolated nucleic acid fragment encoding the amino acid sequence set forth in SEQ ID NO:2, or an enzymatically active fragment thereof;
   (b) an isolated nucleic acid fragment that hybridizes to the nucleic acid fragment of (a) under the conditions of 0.1× SSC, 0.1% SDS at 65° C.;
   (c) an isolated nucleic acid fragment encoding a polypeptide having at least 60% identity with the amino acid sequence set forth in SEQ ID NO:2; and
   (d) an isolated nucleic acid fragment that is complementary to (a), (b), or (c).

2. The isolated nucleic acid fragment of claim 1 as set forth in SEQ ID NO:1.

3. The isolated nucleic acid fragment of claim 1 encoding a fungal DS enzyme obtained from *Magnaporthe grisea*.

4. A chimeric gene comprising the isolated nucleic acid fragment of claim 1 operably linked to suitable regulatory sequences.

5. A transformed host cell comprising a host cell and the chimeric gene of claim 4.

6. The transformed host cell of claim 5 wherein the host cell is a plant cell.

7. The transformed host cell of claim 5 wherein the host cell is *Escherichia coli*.

8. A method of altering the level of expression of a DS enzyme in a host cell comprising:
   (a) transforming a host cell with the chimeric gene of claim 4; and
   (b) growing the transformed host cell of step (a) under conditions that are suitable for expression of the chimeric gene,
resulting in production of altered levels of a DS enzyme relative to expression levels of an untransformed host cell.

9. A method of obtaining a nucleic acid fragment encoding a fungal DS enzyme comprising:
   (a) probing a cDNA or genomic library with 20 or more contigious nucleotides isolated nucleic acid fragment of claim 1;
   (b) identifying a DNA clone that hybridizes with the isolated nucleic acid fragment of claim 1; and
   (c) sequencing the cDNA or genomic fragment that comprises the clone identified in step (b),
wherein the sequenced cDNA or genomic fragment encodes a fungal DS enzyme.

10. A method of obtaining a nucleic acid fragment encoding a fungal DS comprising:
   (a) synthesizing at least one oligonucleotide primer corresponding to 20 or more contigious nucleotides or the isolated nucleic acid fragment of claim 1; and (b) amplifying a cDNA insert present in a cloning vector using the oligonucleotide primer of step (a),
wherein the amplified cDNA insert encodes a fungal DS enzyme.

11. A nucleic acid fragment prepared by the method of claim 9 or 10.

* * * * *

SEQUENCE LISTING

```
(1) GENERAL INFORMATION:

(iii) NUMBER OF SEQUENCES:  10

(2) INFORMATION FOR SEQ ID NO:1:

(i) SEQUENCE CHARACTERISTICS:
          (A) LENGTH:  702 base pairs
          (B) TYPE:  nucleic acid
          (C) STRANDEDNESS:  double
          (D) TOPOLOGY:  linear
```

-continued (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: Magnaporthe grisea DS (xi) SEQUENCE DESCRIPTION: SEQ ID NO:1:

```
ATGCCTTCCA CAGACAGCAT ACCAAAGTCA AATTTTGACG CGATCCCAGA TGTGATCCAA     60

GCATTCAAAA ACGGCGAGTT CGTAGTCGTG CTAGACGACC CCTCGCGCGA GAACGAAGCC    120

GACCTGATCA TCGCCGCCGA GTCGGTAACG ACGGAGCAGA TGGCCTTCAT GGTGCGGCAC    180

TCGTCGGGGC TGATCTGCGC CCCGCTGACG CCGGAGCGCA CCACCGCCCT CGACCTGCCG    240

CAGATGGTGA CGCACAACGC CGACCCGCGC GGCACCGCCT ACACCGTCTC GGTCGACGCC    300

GAGCACCCCT CCACCACCAC CGGCATAAGC GCGCACGACC GCGCCCTCGC CTGCCGCATG    360

CTCGCCGCTC CCGACGCCCA GCCCTCGCAC TTTCGCCGCC CGGGCCACGT CTTCCCCCTC    420

CGCGCCGTCG CGGGCGGCGT CAGGGCCCGC AGGGGCCATA CCGAGGCCGG TGTAGAGCTG    480

TGCAGGCTGG CGGGCAAGAG GCCCGTCGCT GTCATCAGCG AGATTGTCGA CGATGGGCAA    540

GAGGTCGAGG GCCGGGCCGT GCGTGCCGCG CCGGGCATGT TGAGGGGTGA TGAGTGCGTG    600

GCGTTTGCGC GGAGGTGGGG CCTCAAGGTC TGCACTATCG AGGATATGAT TGCCCATGTG    660

GAAAAGACAG AGGGGAAGCT CGAGACGAAT GGGTCGGGTT GA                       702
```

(2) INFORMATION FOR SEQ ID NO:2:

(i) SEQUENCE CHARACTERISTICS:
(A) LENGTH: 233 amino acids
(B) TYPE: amino acid
(C) STRANDEDNESS: Not Relevant
(D) TOPOLOGY: Not Relevant (ii) MOLECULE TYPE: protein (iii) HYPOTHETICAL: NO (iv) ANTI-SENSE: NO (vi) ORIGINAL SOURCE:
(C) INDIVIDUAL ISOLATE: Magnaporthe grisea DS (xi) SEQUENCE DESCRIPTION: SEQ ID NO:2:

```
Met Pro Ser Thr Asp Ser Ile Pro Lys Ser Asn Phe Asp Ala Ile Pro
1               5                   10                  15

Asp Val Ile Gln Ala Phe Lys Asn Gly Glu Phe Val Val Val Leu Asp
            20                  25                  30

Asp Pro Ser Arg Glu Asn Glu Ala Asp Leu Ile Ile Ala Ala Glu Ser
        35                  40                  45

Val Thr Thr Glu Gln Met Ala Phe Met Val Arg His Ser Ser Gly Leu
    50                  55                  60

Ile Cys Ala Pro Leu Thr Pro Glu Arg Thr Thr Ala Leu Asp Leu Pro
65                  70                  75                  80

Gln Met Val Thr His Asn Ala Asp Pro Arg Gly Thr Ala Tyr Thr Val
                85                  90                  95

Ser Val Asp Ala Glu His Pro Ser Thr Thr Thr Gly Ile Ser Ala His
            100                 105                 110

Asp Arg Ala Leu Ala Cys Arg Met Leu Ala Ala Pro Asp Ala Gln Pro
        115                 120                 125
```

```
Ser His Phe Arg Arg Pro Gly His Val Phe Pro Leu Arg Ala Val Ala
    130                 135                 140

Gly Gly Val Arg Ala Arg Arg Gly His Thr Glu Ala Gly Val Glu Leu
145                 150                 155                 160

Cys Arg Leu Ala Gly Lys Arg Pro Val Ala Val Ile Ser Glu Ile Val
                165                 170                 175

Asp Asp Gly Gln Glu Val Glu Gly Arg Ala Val Arg Ala Ala Pro Gly
            180                 185                 190

Met Leu Arg Gly Asp Glu Cys Val Ala Phe Ala Arg Arg Trp Gly Leu
        195                 200                 205

Lys Val Cys Thr Ile Glu Asp Met Ile Ala His Val Glu Lys Thr Glu
210                 215                 220

Gly Lys Leu Glu Thr Asn Gly Ser Gly
225                 230
```

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
        (C) INDIVIDUAL ISOLATE: 5' E. coli DS primer (xi) SEQUENCE DESCRIPTION: SEQ ID NO:3:

ACTCATTTAC CATGGCTCAG ACGCTACTTT CCTC                       34

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
        (C) INDIVIDUAL ISOLATE: 3' E. coli DS primer (xi) SEQUENCE DESCRIPTION: SEQ ID NO:4:

ATCTTACTGT CGACTTCAGC TGGCTTTACG CTC                        33

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
              (C) INDIVIDUAL ISOLATE: 5' E. coli DS primer (xi) SEQUENCE DESCRIPTION: SEQ ID NO:5:

AACTAGATCA GCGGCCGCAG CCACGTTGTG TCTCAAA                                  37

(2) INFORMATION FOR SEQ ID NO:6:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (iv) ANTI-SENSE: NO (vi) ORIGINAL SOURCE:
         (C) INDIVIDUAL ISOLATE: E. coli DS primer (xi) SEQUENCE DESCRIPTION: SEQ ID NO:6:

GACAAACATA GCGGCCGCTG AGGTCTGCCT CGTGAA                                   36

(2) INFORMATION FOR SEQ ID NO:7:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (iv) ANTI-SENSE: NO (vi) ORIGINAL SOURCE:
         (C) INDIVIDUAL ISOLATE: E. coli DS primer (xi) SEQUENCE DESCRIPTION: SEQ ID NO:7:

AACTAGATCA GCGGCCGCTG ACCGTATTAC GAC                                      33

(2) INFORMATION FOR SEQ ID NO:8:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (iv) ANTI-SENSE: NO (vi) ORIGINAL SOURCE:
         (C) INDIVIDUAL ISOLATE: E. coli DS primer (xi) SEQUENCE DESCRIPTION: SEQ ID NO:8:

GACAAACATA GCGGCCGCGT AGTCACACCT TCAGCT                                   36

-continued (2) INFORMATION FOR SEQ ID NO:9:

(i) SEQUENCE CHARACTERISTICS:
       (A) LENGTH:  33 base pairs
       (B) TYPE:  nucleic acid
       (C) STRANDEDNESS:  single
       (D) TOPOLOGY:  linear (ii) MOLECULE TYPE:  other nucleic acid
       (A) DESCRIPTION:  /desc = "primer"

(iii) HYPOTHETICAL:  NO (iv) ANTI-SENSE:  NO (vi) ORIGINAL SOURCE:
       (C) INDIVIDUAL ISOLATE:  5' E. coli DS primer (xi) SEQUENCE DESCRIPTION:  SEQ ID NO:9:

CTACTCATTT CATATGCCTT CCACAGACAG CAT        33

(2) INFORMATION FOR SEQ ID NO:10:

(i) SEQUENCE CHARACTERISTICS:
       (A) LENGTH:  34 base pairs
       (B) TYPE:  nucleic acid
       (C) STRANDEDNESS:  single
       (D) TOPOLOGY:  linear (ii) MOLECULE TYPE:  other nucleic acid
       (A) DESCRIPTION:  /desc = "primer"

(iii) HYPOTHETICAL:  NO (iv) ANTI-SENSE:  NO (vi) ORIGINAL SOURCE:
       (C) INDIVIDUAL ISOLATE:  3' E. coli DS primer (xi) SEQUENCE DESCRIPTION:  SEQ ID NO:10:

CATCTTACTA GATCTTCAAC CCGACCCATT CGTC        34